United States Patent [19]

Fung et al.

[11] 4,268,691

[45] May 19, 1981

[54] SYNTHESIS FOR 2,3-DICHLORO-4-(HYDROXYBENZOYL)-PHENOL

[75] Inventors: Anthony K. L. Fung, Dollard Des Ormeaux; Donald E. Morrison, Otterburn Parks; André G. Pernet, Montreal, all of Canada

[73] Assignee: Abbott Laboratories, North Chicago, Ill.

[21] Appl. No.: 64,948

[22] Filed: Aug. 9, 1979

[51] Int. Cl.³ .............................................. C07C 45/46
[52] U.S. Cl. ................................................... 568/322

[58] Field of Search ............... 260/591; 568/322, 319, 568/323

[56] References Cited

U.S. PATENT DOCUMENTS 4,058,559 11/1977 Jones et al. ......................... 260/591

Primary Examiner—Bernard Helfin
Assistant Examiner—James H. Reamer
Attorney, Agent, or Firm—Paul D. Burgauer; Robert L. Niblack

[57] ABSTRACT

By condensation of anisoyl chloride with 2,3-dichloroanisole under proper conditions, 2,3-dichloro-4-(hydroxybenzoyl)phenol is obtained directly.

8 Claims, No Drawings

SYNTHESIS FOR 2,3-DICHLORO-4-(HYDROXYBENZOYL)PHENOL

DETAILED DESCRIPTION OF THE INVENTION

The diuretics, antihypertensives and uricosuric agents known from U.S. Pat. No. 4,058,559 use the 2,3-dichloro-4-(substituted benzoyl)phenol as an intermediate. These intermediates can easily be converted to the substituted acetic acid derivatives or salts reported in U.S. Pat. No. 4,058,559 by selective alkylation. The current invention is concerned with a more economical way to prepare 2,3-dichloro-4-(hydroxybenzoyl)-phenol.

The new process consists essentially in condensing an anisoyl chloride with an equimolar amount of 2,3-dichloroanisole in the presence of an aprotic solvent and at least one molar equivalent of a Lewis acid essentially at a temperature of between 5° and 30° C., and after at least 6 hours, adding at least one more equivalent of a Lewis acid, and refluxing the mixture for at least 30 minutes. In a preferred embodiment, the Lewis acid used for the two reaction stages is the same, although it is not necessary for the current method which directly produces 2,3-dichloro-4-(hydroxybenzoyl)-phenol. The latter is essentially insoluble in the mentioned aprotic solvent and can be separated therefrom by decantation, filtration, centrifugation or the like. However, the insoluble material collected in this fashion contains usually minor amounts of other insoluble materials such as excess Lewis acid and other by-products. These impurities can easily be removed by treating the solid with concentrated hydrochloric acid and ice. The organic phase then contains the free phenol in a yield of 50% to 70% of theory.

The new method therefore consists essentially of a one-pot synthesis, although the reaction is carried out in two steps. The first step is preferably carried out at room temperature or, at temperatures within a range of between 5° and 30° C., in the presence of at least one molar equivalent of Lewis acid, preferably 1 to 2 molar equivalents. Among the most convenient Lewis acids useful in this method are aluminum chloride, zinc chloride, stannous chloride and the corresponding bromides. The aprotic solvents mentioned above include methylene chloride, ethylene chloride, benzene, carbon disulfide, nitrobenzene, chlorobenzene and the like. In the second step of the reaction, at least one other mole of a Lewis acid, preferably the same Lewis acid as used before and preferably 1 to 5 molar equivalents thereof, are added and the reaction is carried out at reflux temperature. Obviously, at higher temperatures the reaction will be completed faster and depending on the solvent chosen, such higher temperatures are easily obtainable. With methylene or ethylene chlorides, the reflux temperatures are relatively low and this stage of the reaction should be carried out for at least two hours, while in other instances, 30 minutes will be sufficient. An excellent range for this step of the reaction would be between 30 minutes and 4 hours, although longer periods of time are not detrimental to the reaction.

In order to illustrate the method of the present invention, reference is made to the following example, which, however, is not meant to limit the invention in any respect.

EXAMPLE

A mixture of 15.4 g of p-anisoyl chloride and 17.7 g of 2,3-dichloroanisole in 80 ml of dry benzene is cooled at 5° C. After adding 13.3 g of anhydrous aluminum chloride in portions at 5° to 10° C. over a period of five minutes, the cloudy greenish mixture is warmed up to room temperature and then stirred for 48 hours. It is then cooled at 15° C. and 25 ml more of dry benzene is added, followed by the addition of 26.6 g of anhydrous aluminum chloride in portions at 15° C. over a period of five minutes. After the addition is completed, the mixture is stirred at room temperature for 2½ hours, heated to 45° C. for 90 minutes and to 75° C. to 80° C. for one hour. The reaction mixture is then treated with ice and concentrated hydrochloric acid. The organic phase is separated, and the solid residue is washed with boiling dichloroethane to yield 15 g (53% of theory) of crude 2,3-dichloro-4-(4-hydroxybenzoyl)phenol, melting at 208° to 210° C.

The above reaction can be carried out using any other aprotic solvent as reaction medium, replacing the benzene used above. Particularly useful are ethers, ketones and esters, i.e., diethyl ether, acetone, ethyl acetate and the like. Identical results are also obtained when m-anisoyl chloride or o-anisoyl chloride replaces the above used p-anisoyl chloride except that, of course, one obtains the corresponding 2,3-dichloro-4-(3- or 2-hydroxybenzoyl)phenol.

The above example shows that the reaction is initially carried out between 5° C. and about room temperature and subsequently at 45° C. to 90° C. for 2½ hours. Those skilled in the art will recognize that numerous modifications of these temperature levels within the above-mentioned range lead to essentially the same results. For instance, the reaction can first be carried out for 1 to 2 hours at a temperature between 5° and 20° C. and subsequently, depending on the solvent, between 40° C. and the reflux temperature of the aprotic solvent used for 24 hours or more. No advantage is gained by carrying out the reaction beyond two days. The total reaction time usually is no longer than 24 hours and the yields are usually in the neighborhood of 50% to 70% of theory.

Any number of methods can be used to work up the reaction product. In some cases, the reaction product is totally insoluble in the solvent used and the latter can be decanted off and treated with HCl in ice. In other instances, a portion of the reaction product may still be dissolved in the organic solvent used, and as a result, the entire organic solvent mixture containing the reaction product and unused reactants are treated with hydrochloric acid in ice. The Lewis acid will transfer into the aqueous phase while the organic phase contains the desired reaction product. The latter can be isolated therefrom by evaporation of the solvent or other known methods. In either instance, the desired phenolic end product is washed with water and redissolved, for instance, in ether. This organic solvent solution is then treated with charcoal, dried, filtered, and evaporated, leading in many instances, to an oil. When the end product is obtained in this state, trituration with hexane, petroleum ether or the like will often convert the material into a crystallizable solid. Other methods include a brief boiling of the material in a (poly)-chlorinated alkane solvent. However, these steps are not necessary when the described reaction product is used for making the corresponding compound described in U.S. Pat. No. 4,058,559; the organic solution of this intermediate can be reacted directly with an alkyl ester of a haloacetic acid. Otherwise, this reaction is best carried out by dissolving the above identified reaction product in acetone, adding the alkyl haloacetate in the presence of an alkali bicarbonate and refluxing the mixture. This reaction will produce a crude alkyl 2,3-dichloro-4-(hydroxybenzoyl)phenoxyacetate.

We claim:

1. A process of making a 2,3-dichloro-4-(hydroxybenzoyl)phenol consisting essentially in condensing an equimolar amount of an anisoyl chloride and 2,3-dichloroanisole in the presence of 1 to 2 molar equivalents of a Lewis acid, using an aprotic solvent as a reaction medium, at a temperature of between 5° and 30° C. for a period of at least 6 hours, adding 1 to 5 more molar equivalents of a Lewis acid and heating the mixture for a period of at least 30 minutes to a temperature between 40° C. and reflux temperature.

2. The process of claim 1 wherein said Lewis acid in both instances is the same Lewis acid.

3. The process of claim 2 wherein said Lewis acid is aluminum chloride.

4. The process of claim 1 wherein said aprotic solvent is benzene.

5. The process of claim 1 wherein said anisoyl chloride is the p-anisoyl chloride.

6. The process of claim 5 wherein said aprotic solvent is benzene.

7. The process of claim 5 wherein said Lewis acid is aluminum chloride.

8. The process of claim 1 wherein the reaction mixture is subsequently mixed with hydrochloric acid and ice and said diphenol is recovered from the organic phase.

* * * * *